United States Patent
Feng et al.

(10) Patent No.: US 9,012,636 B2
(45) Date of Patent: Apr. 21, 2015

(54) PROCESS FOR THE PREPARATION OF AN OREXIN RECEPTOR ANTAGONIST

(75) Inventors: Yun Shao Feng, Jersey City, NJ (US); Anthony Moses, Cincinnati, OH (US); Yong-Li Zhong, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 18 days.

(21) Appl. No.: 13/880,432

(22) PCT Filed: Oct. 24, 2011

(86) PCT No.: PCT/US2011/057416
§ 371 (c)(1),
(2), (4) Date: Jul. 15, 2013

(87) PCT Pub. No.: WO2012/058129
PCT Pub. Date: May 3, 2012

(65) Prior Publication Data
US 2013/0324728 A1    Dec. 5, 2013

Related U.S. Application Data

(60) Provisional application No. 61/407,955, filed on Oct. 29, 2010, provisional application No. 61/408,098, filed on Oct. 29, 2010.

(51) Int. Cl.
*C07D 401/14* (2006.01)
(52) U.S. Cl.
CPC .................................... *C07D 401/14* (2013.01)
(58) Field of Classification Search
CPC ..................................................... C07D 401/14
See application file for complete search history.

(56) References Cited

U.S. PATENT DOCUMENTS

| 4,340,533 | A | 7/1982 | Rody |
|---|---|---|---|
| 6,469,172 | B2 | 10/2002 | Maligres et al. |
| 6,753,431 | B2 | 6/2004 | Miki et al. |
| 8,242,121 | B2 | 8/2012 | Coleman et al. |
| 2009/0197859 | A1 | 8/2009 | Collantes et al. |

FOREIGN PATENT DOCUMENTS

| WO | WO2009143033 | 11/2009 |
|---|---|---|
| WO | WO 2009143033 A1 * | 11/2009 |

OTHER PUBLICATIONS

Hunig's Base. Chemical Book. "Ethyldiisopropylamine Product Description." Published online: Nov. 10, 2009. Available from: < http://web.archive.org/web/20091110055907/http://www.chemicalbook.com/ChemicalProductProperty_EN_CB4854144.htm >.*
Boggs et al., Efficient Asymmetric Synthesis of N-[(1H)-6-Chloro-2, 3, 4, 9-Tetrahydro-1H-Carbazol-1-yl]-2-Pyridinecarboxamide for Treatment of Human Papillomavirus Infections, Organic Process Research, 2007, vol. 11, pp. 539-545.
Burkhart et al., "Steroselective Synthesis of a C-Glycosidic Analog of N-Glucoasparagine", Angew. Chem, Int. Ed. Engl., 1997, vol. 36, pp. 1191-1192.
Escher et al., "Synthesis of N-1-Carboxy-5-Aminopentyl) Dipeptides as Inhibitors of Angiotensin Converting Enzyme", Angew. Chem. Int. Ed. Engl., 1986, vol. 25, pp. 277-278.
Chen et al., "A Tandem Metal Carbene Cyclization-Cycloaddition Approach to the Pseudolaric Acids", J. Org. Chem., 2003, vol. 368, pp. 4195-4205.
Raghuram et al., "Convenient Conversion of Acid to Weinreb's Amide", Synthetic Communications, 1999, vol. 29, pp. 3215-3219.

* cited by examiner

*Primary Examiner* — Noble Jarrell
*Assistant Examiner* — John S Kenyon
(74) *Attorney, Agent, or Firm* — J. Eric Thies; John C. Todaro

(57) ABSTRACT

The present invention is directed to processes for preparing a pyridyl piperidine compound which is an antagonist of orexin receptors, and which is useful in the treatment or prevention of neurological and psychiatric disorders and diseases in which orexin receptors are involved.

12 Claims, No Drawings

PROCESS FOR THE PREPARATION OF AN OREXIN RECEPTOR ANTAGONIST

CROSS REFERENCE TO RELATED APPLICATIONS

This application is a U.S. National Phase application under 35 U.S.C. §371 of PCT Application No. PCT/US2011/057416, filed Oct. 24, 2011, which claims priority under 35 U.S.C. §119(e) from U.S. Ser. No. 61/407,955, filed Oct. 29, 2010 and 61/408,098 filed Oct. 29, 2010.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

SUMMARY OF THE INVENTION

The present invention is directed to processes for preparing a pyridyl piperidine compound which is an antagonist of orexin receptors, and which is useful in the treatment or prevention of neurological and psychiatric disorders and diseases in which orexin receptors are involved.

DETAILED DESCRIPTION OF THE INVENTION

The present invention is directed to a process for preparing a compound of the formula I:

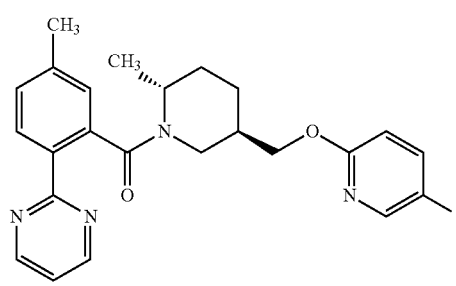

or a pharmaceutically acceptable salt thereof,
which comprises:
contacting a compound of the formula II:

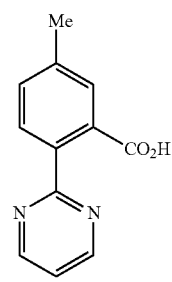

with an activating agent in the presence of an organic base, followed by contacting the resultant product with a compound of the formula III:

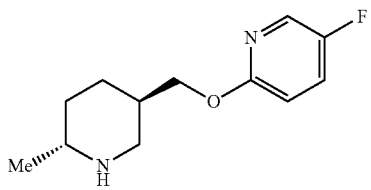

in the presence of 1-propylphosphonic anhydride,
to give the compound of the formula I, or a pharmaceutically acceptable salt thereof.

In a specific embodiment, the present invention is directed to a process for preparing a compound of the formula I:

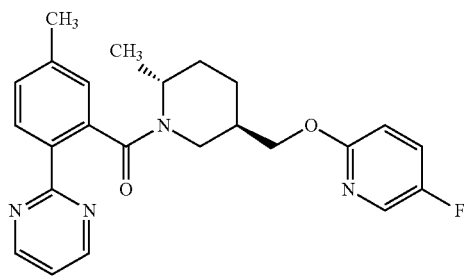

or a pharmaceutically acceptable salt thereof,
which comprises:
contacting a compound of the formula II:

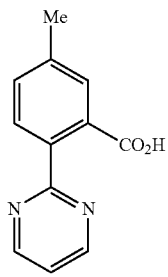

with an activating agent in the presence of a weak organic base,
followed by contacting the resultant product with a compound of the formula III:

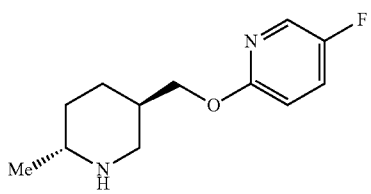

in the presence of 1-propylphosphonic anhydride in an organic solvent,
to give a compound of the formula I, or a pharmaceutically acceptable salt thereof.

The present invention is further directed to a process for preparing a compound of the formula I:

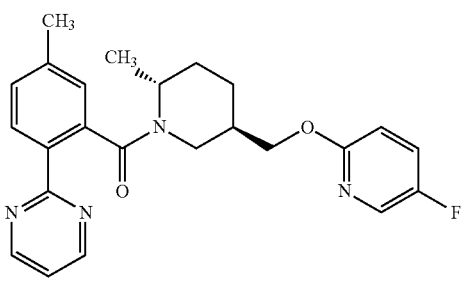

or a pharmaceutically acceptable salt thereof,
which comprises:
contacting a compound of the formula II:

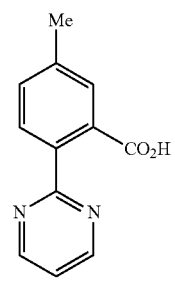

with an activating agent in the presence of a weak organic base,
followed by contacting the resultant product with a compound of the formula III:

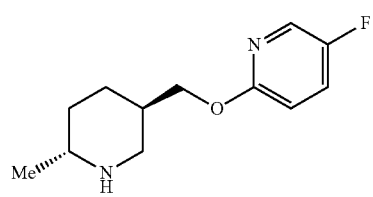

in the presence of a catalytic amount of 1-propylphosphonic anhydride in an amide solvent or acetonitrile, to give the compound of the formula I, or a pharmaceutically acceptable salt thereof.

The present invention is further directed to a process for preparing a compound of the formula I:

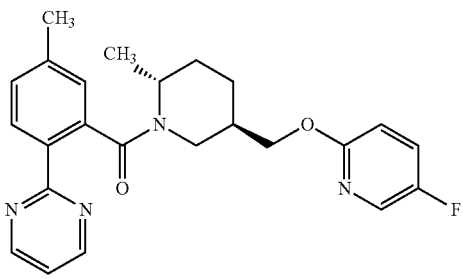

or a pharmaceutically acceptable salt thereof, which comprises:
contacting a compound of the formula II:

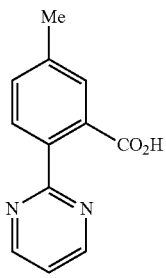

with trimethylacetyl chloride in the presence of 2,6-lutidine, followed by contacting the resultant product with a compound of the formula III:

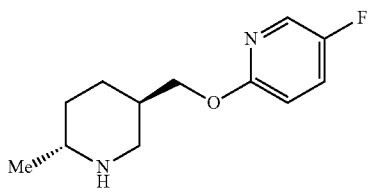

in the presence of a catalytic amount of 1-propylphosphonic anhydride in N,N-dimethylformamide, to give the compound of the formula I, or a pharmaceutically acceptable salt thereof.

The present invention is further directed to a process for preparing a compound of the formula I:

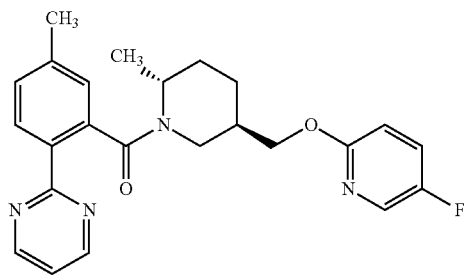

or a pharmaceutically acceptable salt thereof,
which comprises:
contacting a compound of the formula II:

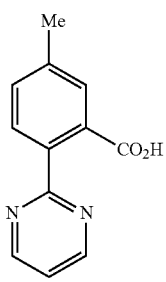

with trimethylacetyl chloride (at greater than 1 equivalents) in the presence of 2,6-lutidine (at greater than 2 equivalents), followed by contacting the resultant product with a compound of the formula III:

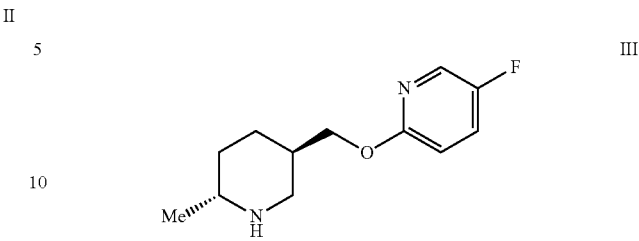

in the presence of 1-propylphosphonic anhydride at less than 10 mol % in N,N-dimethylformamide, to give the compound of the formula I, or a pharmaceutically acceptable salt thereof.

In an alternate embodiment, the present invention is directed to a product prepared by any of the processes disclosed herein.

In an embodiment of the present invention, the activating agent is an acid chloride, chlorofomate, sulfonyl chloride, phosphoryl chloride, $(alkyl)_2POCl$, $(alkylO)_2POCl$, $Ph_2POCl$ and $(PhO)_2POCl$. In an embodiment of the present invention, the activating agent is an alkyl acid chloride. In an embodiment of the present invention, the activating agent is selected from trimethylacetyl chloride, ethyl chloroformate, isobutyl chloroformate, propyl chloroformate, methyl chloroformate and benzyl chloroformate, methanesulfonyl chloride, benzenesulfonyl chloride, tosylsulfonyl chloride. In an embodiment of the present invention, the activating agent is selected from $Ph_2POCl$, $(PhO)_2POCl$, $(MeO)_2POCl$, and $(EtO)_2POCl$. In an embodiment of the present invention, the activating agent is trimethylacetyl chloride.

In an embodiment of the present invention, the resultant product from contacting a compound of the formula II with an activating agent is a mixed anhydride.

In an embodiment of the present invention, the activating agent is added to a reaction mixture comprising the other reagents and starting materials.

In an embodiment of the present invention, the organic base is a weak organic base. In an embodiment of the present invention, the organic base is selected from 2,6-lutidine, 2,4,6-lutidine, diisopropylethylamine (Hunig's base), and triethylamine. In an embodiment of the present invention, the organic base is selected from 2,6-lutidine, 2,4,6-lutidine, and Hunig's base. In an embodiment of the present invention, the organic base is 2,6-lutidine. In an embodiment of the present invention, the organic base is 2,4,6-lutidine.

In an embodiment of the present invention, 1-propylphosphonic anhydride is present at less than a stochiometric amount. The term "catalytic amount" means that 1-propylphosphonic anhydride is present at less than a stochiometric amount. In an embodiment of the present invention, 1-propylphosphonic anhydride is present at less than 50 mol %. In an embodiment of the present invention, 1-propylphosphonic anhydride is present at less than 30 mol %. In an embodiment of the present invention, 1-propylphosphonic anhydride is present at less than 20 mol %. In an embodiment of the present invention, 1-propylphosphonic anhydride is present at less than 15 mol %. In an embodiment of the present invention, 1-propylphosphonic anhydride is present at less than 10 mol %. In an embodiment of the present invention, 1-propylphosphonic anhydride is present at less than 5 mol %.

In an embodiment of the present invention, the step of contacting the compound of the formula II with an activating agent in the presence of a weak organic base is conducted in an amide solvent or acetonitrile solvent. An amide solvent is an organic solvent containing an amide functionality.

In an embodiment of the present invention, the process is conducted in an amide solvent. In an embodiment of the present invention, the step of contacting the mixed anhydride with a compound of formula III to give a compound of formula I is conducted in an amide solvent. An amide solvent is an organic solvent containing an amide functionality.

In an embodiment of the present invention, the amide solvent is selected from the group consisting of: formamide, N-methylformamide, N,N-dimethylformamide, acetamide, N-methylacetamide, N,N-dimethylacetamide, N,N,N',N'-tetramethylurea, 2-pyrrolidone, and N-methylpyrrolidone.

In an embodiment of the present invention, the amide solvent is N,N-dimethylformamide, N,N-dimethylacetamide or N-methylpyrrolidone.

In an embodiment of the present invention, the process is conducted at a temperature below 100° C. In an embodiment of the present invention, the process is conducted at a temperature below 75° C. In an embodiment of the present invention, the process is conducted at a temperature below 50° C. In an embodiment of the present invention, the process is conducted at a temperature of about room temperature.

In an alternate embodiment, the present invention is directed to a process for preparing a compound of the formula A-2:

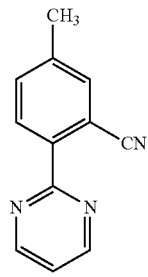

A-2 or a salt thereof,
which comprises:
contacting a compound of the formula II-a:

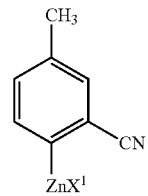

II-a with a compound of the formula III-a:

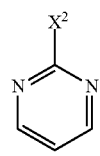

III-a wherein $X^1$ is halo; and $X^2$ is halo or $R^1S(O)_2$—O—;
wherein $R^1$ is fluoro, halo$C_{1-6}$alkyl-, phenyl-, or $C_{1-6}$alkylphenyl-;

in the presence of a transition metal source, and optionally a ligand, to give the compound of the formula A-2, or a salt thereof.

In an aspect of this alternate embodiment, $X^1$ is bromo, chloro, or iodo; $X^2$ is bromo, chloro, iodo, $FSO_2$—O—, or $CF_3SO_2$—O—. In one class of this alternate embodiment, $X^1$ is chloro and $X^2$ is chloro. In one class of this alternate embodiment, $X^1$ is bromo and $X^2$ is bromo. In one class of this alternate embodiment, $X^1$ is iodo and $X^2$ is iodo.

In an aspect of this alternate embodiment, the transition metal source is a palladium source or a nickel source.

In an aspect of this alternate embodiment, the palladium or nickel source is tetrakis(triphenylphosphine)nickel(0), nickel (II) di-acetylacetone, bis(cyclooctadiene)nickel(0), nickel (II) chloride, bis(dibenzylideneacetone)palladium(0), tetrakis(triphenylphosphine)-palladium(0), bis(acetonitrile) palladium(II) chloride, bis(triphenylphosphine)palladium (II) chloride, [1,4-bis(diphenylphosphine)butane]palladium (II) dichloride, [1,2-bis(diphenyl-phosphine)ethane] palladium(II) dichloride, [1,2'-bis(diphenylphosphino) ferrocene]-palladium(II) diacetate, [1,1'-bis (diphenylphosphino)ferrocene]palladium(II) dichloride, bis (triphenyl-phosphine)palladium(II) chloride, palladium(II) acetate, palladium(II) chloride, palladium/carbon or mixtures thereof.

In an aspect of this alternate embodiment, the transition metal source is a palladium source, wherein the palladium source is tetrakis(triphenylphosphine)palladium(0), bis(acetonitrile)-palladium(II) chloride, bis(triphenylphosphine) palladium(II) chloride, [1,4-bis(diphenyl-phosphine)butane] palladium(II) dichloride, [1,2-bis(diphenylphosphine) ethane]-palladium(II) dichloride, [1,2'-bis (diphenylphosphino)ferrocene]palladium(II) diacetate, [1,1'-bis(diphenyl-phosphino)ferrocene]palladium(II) dichloride, bis(triphenylphosphine)palladium(II) chloride, palladium (II) acetate, palladium(II) chloride, palladium/carbon or mixtures thereof. In one class of this alternate embodiment, the transition metal source is a palladium source, wherein the palladium source is palladium(II) acetate or palladium(II) chloride. In one class of this alternate embodiment, the transition metal source is a palladium source, wherein the palladium source is palladium(II) acetate.

In an aspect of this alternate embodiment, the transition metal source is a nickel source, wherein the nickel source is tetrakis(triphenylphosphine)nickel(0), nickel(II) di-acetylacetone, bis(cyclooctadiene)nickel(0), nickel(II) chloride or mixtures thereof.

In an aspect of this alternate embodiment, the ligand is a tri($C_{1-6}$alkyl)phosphine, a tri(aryl)phosphine, a di($C_{1-6}$alkyl) arylphosphine, a bidentate phosphine or mixtures thereof. Non-limiting examples of the ligand include dibenzylideneacetone, triphenylphosphine, 1,4-bis(diphenylphosphine)butane, 1,2-bis(diphenylphosphine)ethane, 1,2'-bis(diphenylphosphino)-ferrocene, 1,1'-bis(diphenylphosphino) ferrocene, acetylacetone, tri(n-butyl)phosphine, tri(t-butyl) phosphine, diphenyl(t-butyl)phosphine, cyclooctadiene or mixtures thereof. In one class, the ligand is tri(n-butyl)phosphine.

In an aspect of this alternate embodiment, the transition metal source is in an amount of 0.05 to 5.0 mole % relative to the compound of formula I. In one class of this alternate embodiment, the transition metal source is an amount of 0.05 to 1.0 mole %.

In an aspect of this alternate embodiment, the reaction is conducted in a solvent. In one class of this alternate embodiment, the solvent is an aprotic solvent. Non-limiting examples of aprotic solvents include tetrahydrofuran, methyl-tetrahydrofuran, dioxane, methyl t-butyl ether, methyl cyclohexyl ether or mixtures thereof. In one class of this alternate embodiment, the aprotic solvent is tetrahydrofuran.

In an aspect of this alternate embodiment, the reaction temperature is in the range of about 25-85° C. In a class of this embodiment, the reaction temperature is in the range of about 25-60° C. In a class of this embodiment, the reaction temperature is in the range of about 40-50° C.

In an aspect of this alternate embodiment, the reaction is conducted in the presence of a transition metal source, wherein the transition metal source is a palladium source, and a ligand, wherein the ligand is a tri($C_{1-6}$alkyl)phosphine. In one class of this alternate embodiment, the palladium source is palladium(II) acetate. In one class of this embodiment, the ligand is tri(n-butyl)phosphine. In one class of this alternate embodiment, the palladium source is palladium(II) acetate and the ligand is tri(n-butyl)phosphine.

A specific embodiment of this alternate embodiment is directed to a process for preparing a compound of the formula A-3:

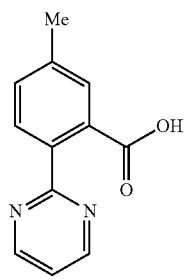

A-3 or a salt thereof,
which comprises:

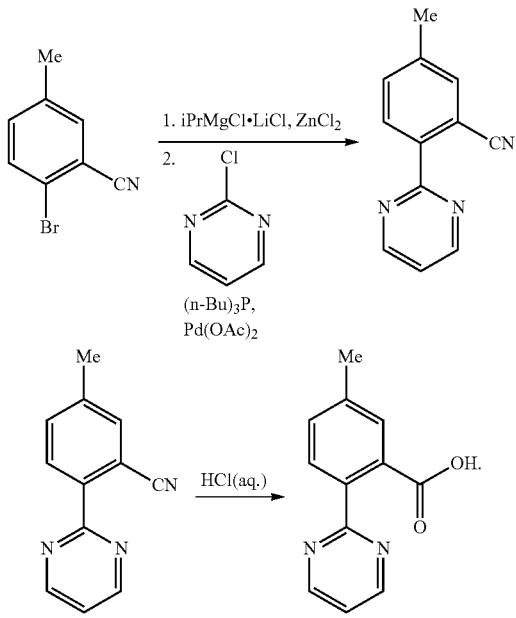

In another alternate embodiment, the present invention is directed to a process for preparing a compound of the formula I:

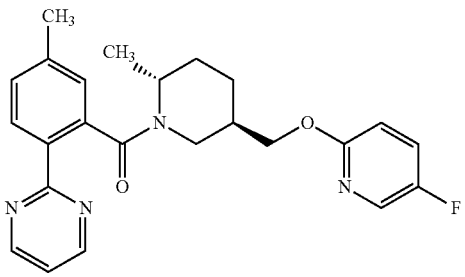

I or a pharmaceutically acceptable salt thereof,
which comprises:
crystallizing the compound of the formula I from an aromatic solvent selected from the group consisting of tert-butylbenzene, o-xylene, p-xylene, cumene, ethylbenzene and toluene, and isolating the compound of formula I, or a pharmaceutically acceptable salt thereof.

In an aspect of this alternate embodiment, the aromatic solvent is selected from the group consisting of tert-butylbenzene, o-xylene, p-xylene, cumene, ethylbenzene and toluene, or an aromatic solvent which additionally comprises heptane. In an aspect of this alternate embodiment, the aromatic solvent is toluene. In an aspect of this alternate embodiment, the aromatic solvent is tert-butylbenzene. In an aspect of this alternate embodiment, the compound of formula I is provided in a purity of greater than 90%. In an aspect of this alternate embodiment, the compound of formula I is provided in a purity of greater than 95%. In an aspect of this alternate embodiment, the compound of formula I is provided in a purity of greater than 97%. In an aspect of this alternate embodiment, the compound of formula I is provided in a purity of greater than 98%. In an aspect of this alternate embodiment, the compound of formula I is provided in a purity of greater than 99%. In an aspect of this alternate embodiment, the compound of formula I is provided in a purity of greater than 99.5%. In an aspect of this alternate embodiment, the compound of formula I is provided in a purity of greater than 99.9%. In an alternate embodiment, the present invention is directed to a product prepared by such process.

The subject compound of the formula I is disclosed as an antagonist of orexin receptors in PCT Patent Publication WO 2008/147518. Certain processes to prepare the subject compound of the formula I are disclosed in WO 2009/143033. Relative to the processes disclosed in WO 2009/143033, the present invention provides an improved process for the efficient, scalable, chromatography-free and cost-effective preparation of the formula I in three steps. Whereas the processes disclosed in WO 2009/143033 utilizes excess equivalents of $T_3P$ (1-propylphosphonic anhydride), the present invention employs lower amounts of $T_3P$ to give higher isolated yield of the subject compound.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the compound with the designation of specific stereochemistry. When the compounds of the present invention contain one chiral center, the term "stereoisomer" includes both enantiomers and mixtures of enantiomers, such as the specific 50:50 mixture referred to as a racemic mixtures.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Several methods for preparing the compounds of this invention are illustrated in the following Schemes and Examples. Starting materials are made according to procedures known in the art or as illustrated herein. The following abbreviations are used herein: 2-MeTHF: 2-methyltetrahydrofuran; Ac: acetyl; Ar: aryl; AY: assay yield; Bn: benzyl; Boc: tert-butyloxy carbonyl; $Boc_2O$: di-tert-butyldicarbonate; BSA: bovine serum albumin; Cbz: carbobenzyloxy; CDI: carbonyl diimidazole; CSA: camphor sulfonic acid; DEAD: diethylazodicarboxylate; DCE: dichloroethane; DCM: dichloromethane; DIPEA: N,N-diisopropylethylamine; DMF: N,N-dimethylformamide; DMSO: dimethylsulfoxide; EDC: N-(3-dimethylaminopropyl)-N'-ethylcarbodiimide; Et: ethyl; EtOH: ethanol; $Et_3N$: triethylamine; GC-FID: gas chromatography-flame ionization detector; HOBT: hydroxybenzotriazole hydrate; HPLC: high performance liquid chromatography; LC-MS: liquid chromatography-mass spectrometry; LRMS: low resolution mass spectrometry; Me: methyl; MTBE: methyl tert-butyl ether; NAD: nicotinamide adenine dinucleotide; NMP: N-methylpyrrolidone; $PdCl_2$(dppf)-$CH_2Cl_2$: [1,1'-Bis(diphenylphosphino)ferrocene] dichloropalladium(II) dichloromethane; Ph: phenyl; PhMe: toluene; PLP: pyridoxal-5' phosphate; rt: room temperature; $SOCl_2$: thionyl chloride; $T_3P$: 1-propylphosphonic anhydride; t-Bu; tert-butyl; TsCl: tosyl chloride; TFA: trifluoroacetic acid; THF: tetrahydrofuran. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes and examples may be varied to facilitate the reaction or to avoid unwanted reaction products. The following examples are provided so that the invention might be more fully understood. These examples are illustrative only and should not be construed as limiting the invention in any way.

Example 1

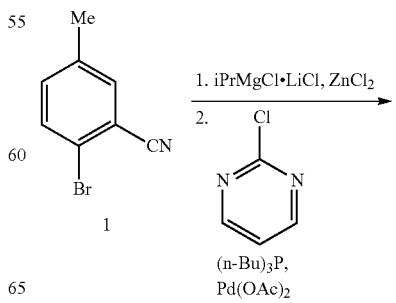

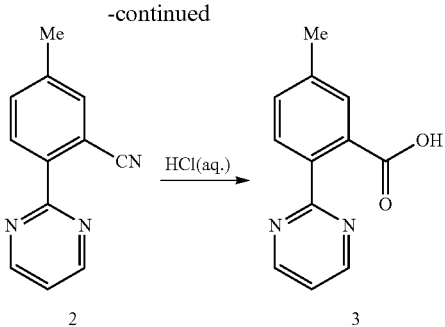

Methyl-2-(pyrimidin-2-yl)benzonitrile (2)

To a 500 mL three neck round bottom flask, equipped with an overhead stirrer, thermocouple and nitrogen inlet and dropped funnel, was charged 2-bromo-5-methylbenzylnitrile 1 (20.00 g) and THF (60 mL, 3 V) and was cooled to −15° C. 1.3 M of i-PrMgCl.LiCl (110.0 mL, 1.4 equiv) was slowly added at −15 to −12° C. The reaction mixture was stirred at −15 to −12° C. for 3.5 h (>99 A % conversion). 15.45 g of anhydrous $ZnCl_2$ (1.1 equiv, powder) was added to the Grignard reagent at −12° C. in one portion. The reaction was exothermic raising the temperature of the reaction mixture to 0° C. The reaction mixture was stirred at −3 to 2° C. for 0.5 h and slowly warmed to rt over 0.5 h. The reaction mixture became a homogenous solution and then 2-chloropyrimidine (15.37 g) was added.

To a slurry of 1 mol % $Pd(OAc)_2$ (0.229 g), 4 mol % $(n-Bu)_3P$ (0.826 g or 1.02 mL) in THF (8 mL) was added 2.0 M of BuMgCl (1.02 mL) THF solution to become yellow cloudy solution. The resulting catalyst solution was added to the reaction mixture. The resulting mixture was heated at 55° C. for 17 h: (98 A % conversion). The reaction mixture was solvent-switched to isopropyl alcohol (140 mL, total volume) at 40-45° C. Then 5 wt % $NH_4Cl$ aqueous solution (70 mL) was added dropwise at 15 to 20° C. The resulting slurry was aged at 10° C. for 5 h. The crystalline solid was collected by filtration, rinsed with cold isopropyl alcohol/water (1:1, 35 mL), and n-heptane (30 mL), dried under vacuum with nitrogen sweep and gave desired product 2 (17.33 g, 87% isolated yield, 99.5 LCAP purity).

HPLC Method

Column: Zorbax Eclipse Plus C18 50×4.6 mm, 1.8 μm particle size,

Column Temp.: 25° C.; Flow Rate: 1.5 mL/min; Detection: 230 nm; Mobile Phase: A: Water 0.1% $H_3PO_4$, Acetonitrile

|  | Time | A |
|---|---|---|
| Mobile Phase Program: | | |
|  | 0 | 90% |
|  | 5 min | 5% |
|  | 6 min | 5% |
|  | 6.1 min | 90% |
|  | 8 min | 90% |
| Compound 2: | 3.19 min | |

5-Methyl-2-(pyrimidin-2-yl)benzoic Acid (3)

To a 150 mL three neck round bottom flask, equipped with overhead stirrer, thermocouple and HCl-scrub, was charged 12 N HCl solution (17.1 mL, 8 equiv) and was cooled to 10° C. Acetonitrile (5 mL, 1 V) was added. Then, biaryl nitrile 2 (5.00 g) was added in portion at 10-15° C. The reaction mixture was aged at 10-15° C. for 2 h, and slowly warmed to 22° C. and aged at the same temperature for 48 h (100 A % conversion). The reaction mixture was cooled to 0° C. 20 wt % of NaCl solution was added dropwise. The resulting slurry was aged at 0-5° C. for 6 h. The crystalline solid was collected by filtration, rinsed with water and cold EtOAc, dried under vacuum with nitrogen sweep to give product 3 (4.95 g, 90% isolated yield, 98.9 LCAP purity).

HPLC Method

Column: Zorbax Eclipse Plus C18 50×4.6 mm, 1.8 μm particle size,

Column Temp.: 25° C.; Flow Rate: 1.5 mL/min; Detection: 230 nm; Mobile Phase: A: Water 0.1% $H_3PO_4$, B: Acetonitrile

|  | Time | A |
|---|---|---|
| Mobile Phase Program: | | |
|  | 0 | 90% |
|  | 5 min | 5% |
|  | 6 min | 5% |
|  | 6.1 min | 90% |
|  | 8 min | 90% |
| Compound A-3: | 2.19 min | |

Example 2

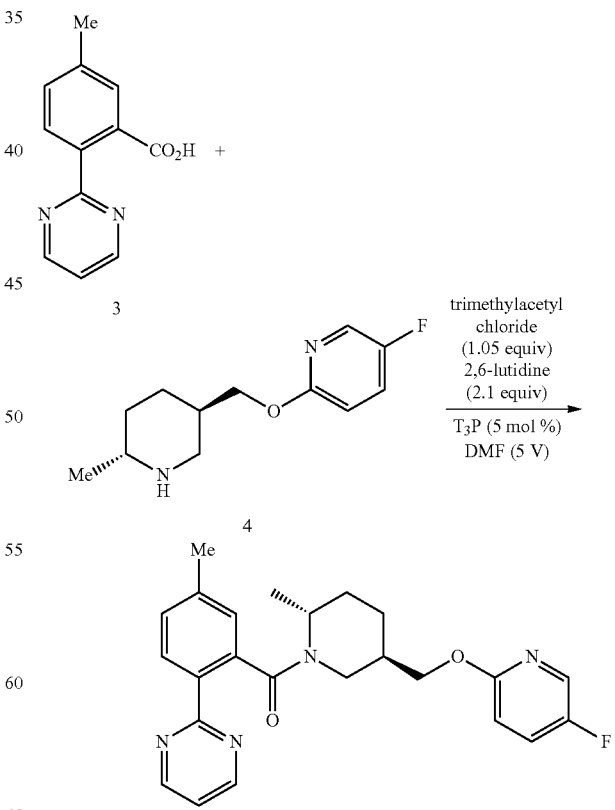

2-{2-[((2R,5R)-5-{[(5-Fluoropyridin-2-yl)oxy]methyl}-2-methylpiperidin-1-yl)carbonyl]-4-methylphenyl}pyrimidine (5)

To a 2 L round bottom flask, equipped with over head stirrer, thermocouple, dropping funnel, and nitrogen inlet, was charged biaryl acid 3 (43.10 g, 1.05 equiv), 2,6-dimethylpyridine (23.15 mL, 1.05 equiv) and DMF (250 mL, 5 V) and was cooled to 5° C. Then, trimethyl acetyl chloride (Piv-Cl) (24.45 mL) was slowly added at 5-10° C. The reaction was stirred at 10° C. for 0.5 h. Amine-HCl salt 4 (50.00 g) and 50 wt % $T_3P$ in DMF (5.96 g, 5 mol %) were added at 10-15° C., respectively. The reaction mixture was stirred at 20-25° C. for 1-2 h (typical >76 A % conversion), 2,6-lutidine (22.05 mL, 1.0 equiv) was slowly added over 0.5 h, the reaction mixture was stirred at rt for 3-5-h (>95 A % conversion). The reaction can be also carried out as follows. To a 2 L round bottom flask, equipped with overhead stirrer, thermocouple, dropping funnel, and nitrogen inlet, was charged biaryl acid 3 (43.10 g, 1.05 equiv), 2,6-dimethylpyridine (45.2 mL, 2.05 equiv), amine-HCl salt 4 (50.00 g), 50 wt % $T_3P$ in DMF (5.96 g, 5 mol %) and DMF (250 mL, 5 V) and the resulting mixture was cooled to 15° C. Then, Piv-Cl (24.45 mL) was slowly added at 15-25° C. After complete addition of Piv-Cl, the reaction mixture was aged at 20-25° C. for 3-5 h (>95 A % conversion).

10 mol % of 2,6-lutidine (2.21 mL) and 10 mol % of Piv-Cl (2.45 mL) were added at rt, respectively. The reaction mixture was stirred at room temperature for 8-16 h (98.5 A % conversion).

The reaction mixture was diluted with toluene (500 mL, 10 volume) and water (250 mL, 5 V) at 10-20° C. The reaction mixture was stirred at 10-20° C. for 0.5 h. After phase separation, the aqueous layer was extracted with toluene (250 mL×1, 5 volumes). The combined organic layer was washed with water (200 mL×1, 4 volumes), 1 N NaOH (200 mL×1, 4 volumes), and 16% brine (100 mL×1, 2 volumes).

The resulting toluene solution was filtered through 20 wt % of Aquagard activated carbon (14.8 g, equal to 20 wt % of assay product), which was held on solka flock (16 g). The cake was rinsed with toluene (400 mL, 8 volumes)

The combined filtrates were concentrated to 150 mL (total volume). At this point, tert-butylbenzene (70 mL) was added dropwise. The resulting solution was solvent-switched to tert-butylbenzene (200 mL, total volume). Crystalline solid 5 was formed during solvent-switch. The resulting slurry was heated to 90-95° C. to become homogenous solution. The resulting solution was cooled to 80° C. and was seeded with 2% desired crystalline form of 5. The slurry was aged at 80° C. for 2 h, and then was slowly cooled to 60° C. over 10 h, and from 60 to 20° C. over 10 h. The resulting slurry was aged at 20 for 24-48 h. The crystalline solid was collected by filtration, rinsed with tert-butylbenzene (50 mL), n-heptane (100 mL), dried under vacuum with nitrogen sweep and gave 2-{2-[((2R,5R)-5-{[(5-fluoropyridin-2-yl)oxy]methyl}-2-methylpiperidin-1-yl)carbonyl]-4-methylphenyl}pyrimidine (5) (66.85 g, 88% isolated yield).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A process for preparing a compound of the formula I:

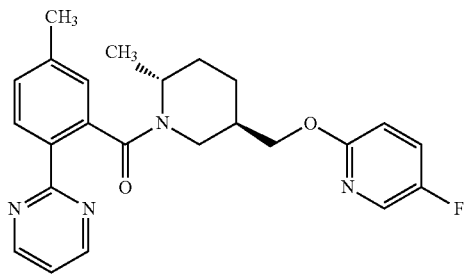

or a pharmaceutically acceptable salt thereof,
which comprises:
contacting a compound of the formula II:

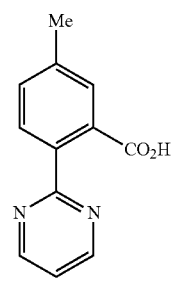

with trimethylacetyl chloride in the presence of an organic base,
followed by contacting the resultant product with a compound of the formula III:

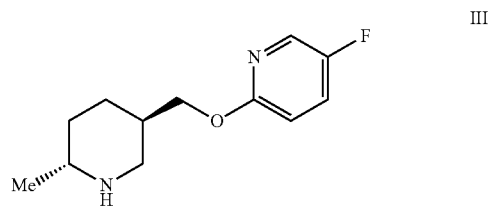 [SMILES: C[C@@H]1CC[C@@H](COc2ccc(F)cn2)CN1]

in the presence of 1-propylphosphonic anhydride, wherein the 1-propylphosphonic anhydride is present at less than a stochiometric amount,
to give the compound of the formula I.

2. The process of claim 1 wherein the organic base is a weak organic base.

3. The process of claim 1 wherein the organic base is selected from 2,6-lutidine, 2,4,6-lutidine, and Hunig's base.

4. The process of claim 1 wherein 1-propylphosphonic anhydride is present at less than 10 mol %.

5. The process of claim 1 wherein the process is conducted in an amide solvent or acetonitrile.

6. The process of claim 5 wherein the process is conducted in an amide solvent which is selected from the group consisting of: formamide, N-methylformamide, N,N-dimethylformamide, acetamide, N-methylacetate, N,N-dimethylacetamide, N,N,N',N'-tetramethylurea, 2-pyrrolidone, and N-methylpyrrolidone.

7. The process of claim 6 wherein the amide solvent is N,N-dimethylformamide.

8. The process of claim 5 wherein the process is conducted in acetonitrile.

9. A process for increasing the purity of a compound of the formula I:

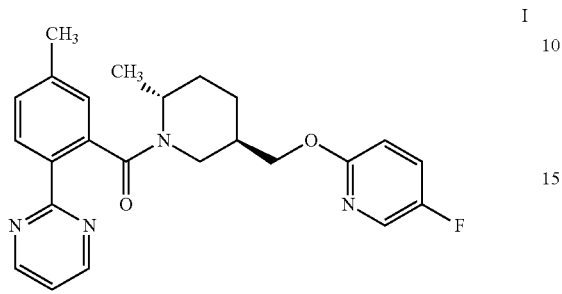

or a pharmaceutically acceptable salt thereof, which comprises:
crystallizing the compound of the formula I from a solvent which comprises an aromatic solvent selected from the group consisting of tert-butylbenzene, o-xylene, p-xylene, cumene, ethylbenzene and toluene.

10. The process of claim 9 wherein the aromatic solvent is tert-butylbenzene.

11. The process of claim 9 wherein the aromatic solvent is toluene.

12. The process of claim 11 wherein the aromatic solvent additionally comprises heptane.

\* \* \* \* \*